United States Patent [19]

Dudar et al.

[11] Patent Number: 5,324,948
[45] Date of Patent: Jun. 28, 1994

[54] AUTONOMOUS MOBILE ROBOT FOR RADIOLOGIC SURVEYS

[75] Inventors: Aed M. Dudar; David G. Wagner, both of Augusta, Ga.; Gregory D. Teese, Aiken, S.C.

[73] Assignee: The United States of America as represented by the United States Department of Energy, Washington, D.C.

[21] Appl. No.: 966,925

[22] Filed: Oct. 27, 1992

[51] Int. Cl.$^5$ ............................................. G01V 5/00
[52] U.S. Cl. ..................................... 250/379; 250/253
[58] Field of Search ............ 250/379, 253, 255, 336.1, 250/301, 302

[56] References Cited

U.S. PATENT DOCUMENTS

| | | | |
|---|---|---|---|
| 4,455,551 | 6/1984 | Lemelson | 340/539 |
| 4,709,265 | 11/1987 | Silverman et al. | 358/108 |
| 5,025,150 | 6/1991 | Oldham et al. | 250/253 |

*Primary Examiner*—Paul M. Dzierzynski
*Assistant Examiner*—Richard Hanig
*Attorney, Agent, or Firm*—Brian R. Tumm; Harold M. Dixon; William R. Moser

[57] ABSTRACT

An apparatus for conducting radiologic surveys. The apparatus comprises in the main a robot capable of following a preprogrammed path through an area, a radiation monitor adapted to receive input from a radiation detector assembly, ultrasonic transducers for navigation and collision avoidance, and an on-board computer system including an integrator for interfacing the radiation monitor and the robot. Front and rear bumpers are attached to the robot by bumper mounts. The robot may be equipped with memory boards for the collection and storage of radiation survey information. The on-board computer system is connected to a remote host computer via a UHF radio link. The apparatus is powered by a rechargeable 24-volt DC battery, and is stored at a docking station when not in use and/or for recharging. A remote host computer contains a stored database defining paths between points in the area where the robot is to operate, including but not limited to the locations of walls, doors, stationary furniture and equipment, and sonic markers if used. When a program consisting of a series of paths is downloaded to the on-board computer system, the robot conducts a floor survey autonomously at any preselected rate. When the radiation monitor detects contamination, the robot resurveys the area at reduced speed and resumes its preprogrammed path if the contamination is not confirmed. If the contamination is confirmed, the robot stops and sounds an alarm.

18 Claims, 4 Drawing Sheets

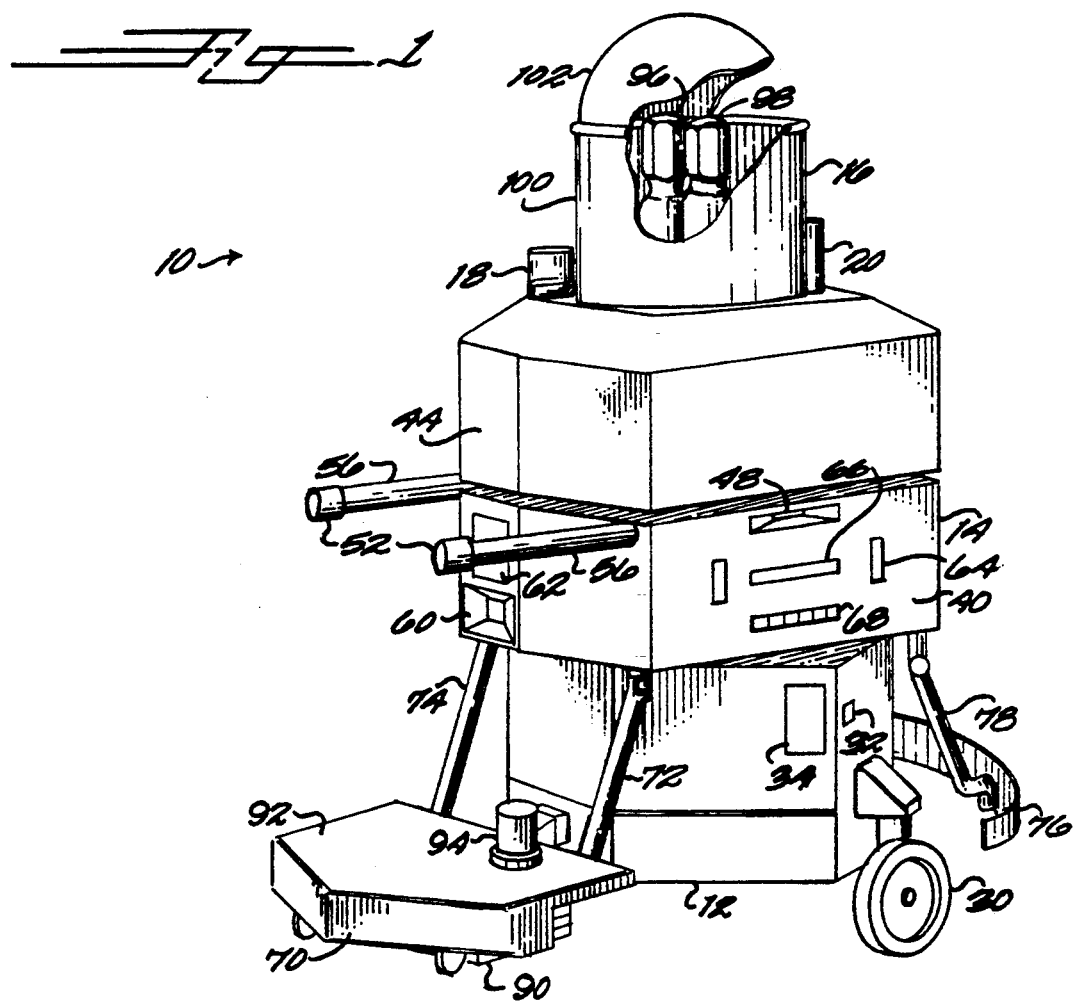

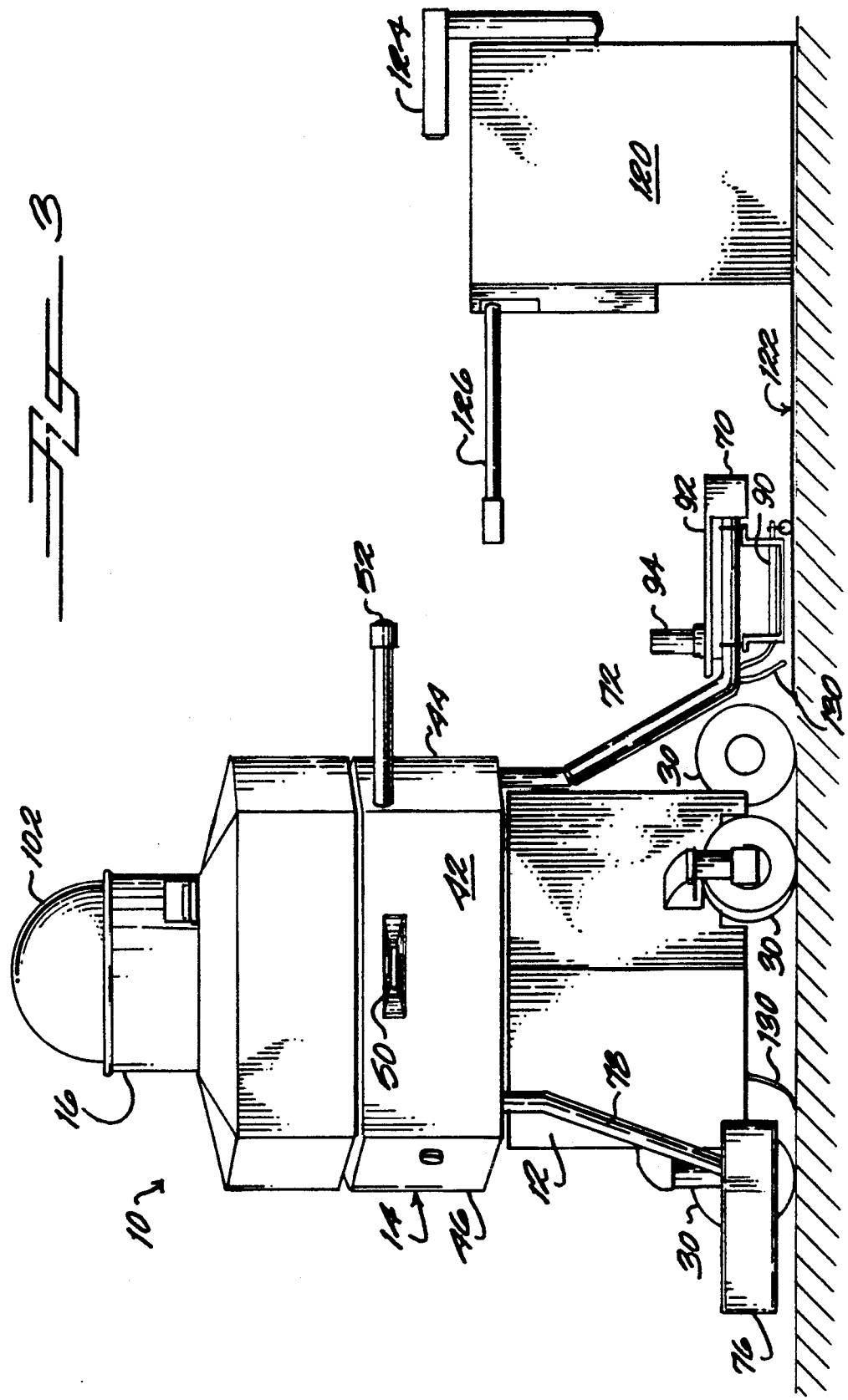

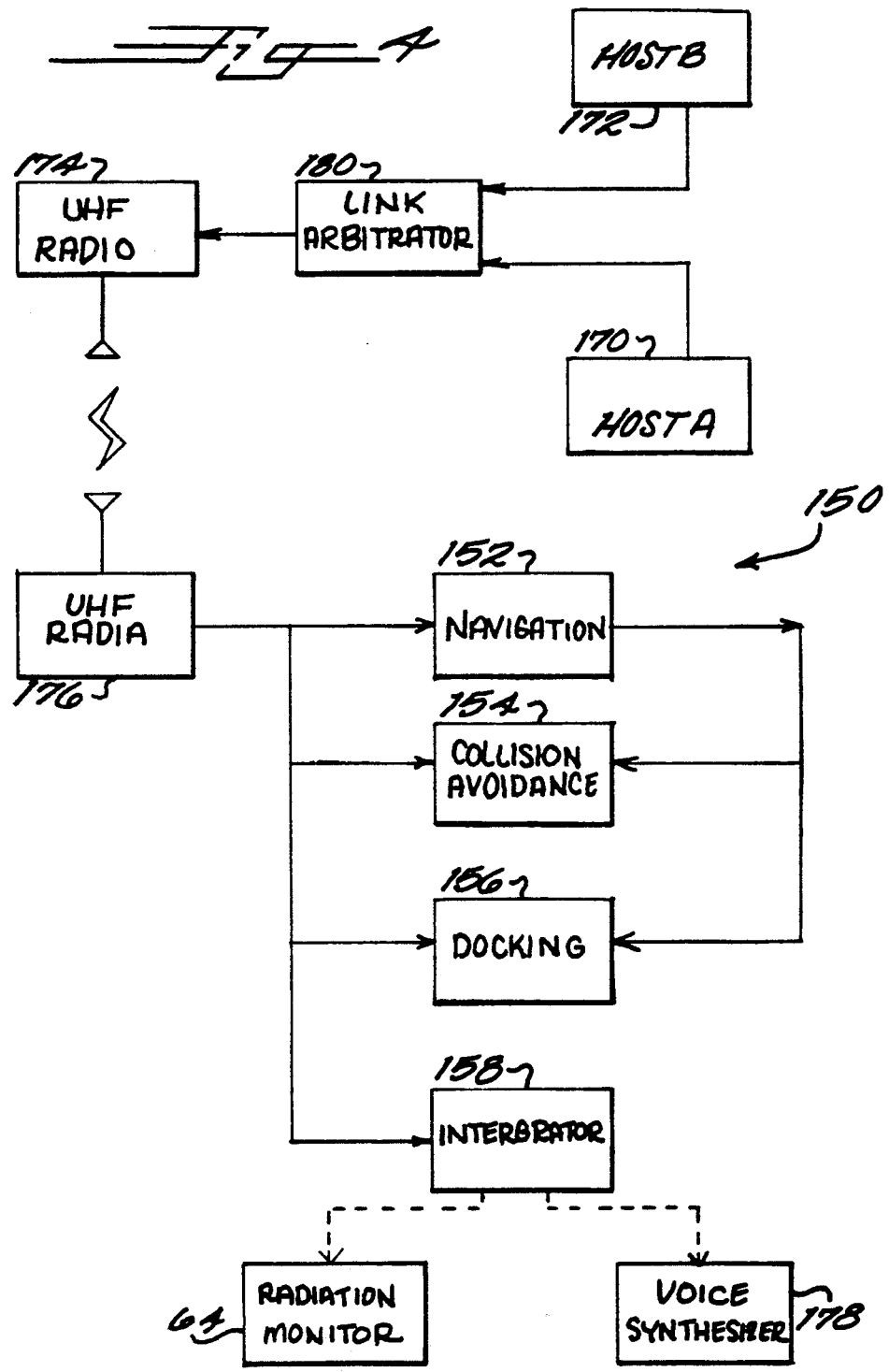

AUTONOMOUS MOBILE ROBOT FOR RADIOLOGIC SURVEYS

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to remote radiologic surveying. In particular, the present invention relates to radiologic surveys done by autonomous robots.

2. Discussion of Background

At present radiologic surveying of an area is usually done either by placing radiological instrumentation in that area to monitor the radiation levels or by manually making radiologic measurements using several standard techniques on specific surfaces in the area.

When an area is known to be contaminated, a health physicist will make measurements of background and the radiation coming from surfaces and take samples of contaminants on those surfaces for analysis. If that surface is to be decontaminated, it will be sampled periodically during the decontamination process until all traces of contaminants are removed. The sampling may be directed to random parts of the surface or may involve measurement of all parts of the decontaminated surface.

If the area is one where radioisotopes are handled routinely but contamination is not usually present, the far more common practice is to take radiological samples for measurements on a statistical basis; that is, small portions of the surfaces are sampled at random and the overall condition of the surface is inferred from the results of these measurements. Routine monitoring may also include floor surveys, where the floor is manually scanned at a rate of 1" per second using hand-held portable monitors.

Random surveys sample only a small portion of a potentially-contaminated surface. Obviously, if contamination is present in an area that is not selected for sampling, it will go undetected and can be spread by personnel moving through and about the area. Sampling typically involves wiping the surface with a paper disk and analyzing that disk for contamination, which sample is called a smear sample and which technique is called "smearing." This techniques is only capable of locating transferable or loose contamination.

In addition, when the chance of finding contamination in an area is very low, 100 percent sampling is unrealistic because of the time and labor involved. Manual scanning is labor-intensive, cumbersome and inefficient.

The problems associated with manual scanning could be largely eliminated by an automated scanning system, preferably a system that alerts personnel to the presence of contamination. Monitoring devices that provide an alarm in the presence of a hazard are known. For example, a remotely-operated system monitors a variety of hazardous conditions and enunciates the presence of a hazard in synthesized human speech (Lemelson, U.S. Pat. No. 4,455,551). Remotely-controlled devices for environmental monitoring are also available. However, all known devices require a human operator using stereoptic television cameras to direct from a remote location the activities of a vehicle. See also Silverman, et al., U.S. Pat. No. 4,709,265. Measuring radiation over 100 percent of an area using such a device is very tedious for the operator because measurements should be done no faster than approximately 1"/sec (2.5 cm/sec). There is a need for an effective and autonomous scanning system, that is, a system that measures radiation without human supervision at least until contamination is found.

SUMMARY OF THE INVENTION

According to its major aspects and broadly stated, the present invention is an apparatus for conducting radiologic surveys. It comprises in the main a robot capable of following a preprogrammed path through an area, a radiation monitor carried by the robot, ultrasonic transducers for navigation and collision avoidance, and an on-board computer system including an integrator for interfacing the activities of the radiation monitor, the robot and auxiliary devices.

To program the robot, the operator first defines points in the area where it is to operate, including but not limited to the locations of walls, doors, stationary furniture and equipment, and sonic markers if used. Point-to-point path programs are written and assembled into "action files." When the operator programs the robot to move from point "a" to point "b," the program sorts through its database to find the most efficient action file, or combination of files, between the points.

The robot has two modes of operation, manual and automatic. In manual mode, an operator directs the motion of the robot via a joystick. In automatic mode, the robot executes a predefined path downloaded from a remote host computer to the on-board computer system via a UHF radio link. Once a path is downloaded, the robot acts autonomously until it reaches the end of the path.

The integrator constantly monitors the outputs of the radiation monitor. If the radiation monitor senses contamination, the integrator directs the robot to stop and flash a strobe light, back up a short distance and resurvey the area at reduced speed to confirm the presence of contamination. If no contamination is found on the second pass, the robot resumes its preprogrammed path. If the presence of contamination is confirmed, the robot stops again, flashes the strobe light continuously and sounds an audible alarm. When an operator acknowledges the alarm, the robot backs up and activates a voice synthesizer that outputs a message indicating the type of contamination detected (alpha or beta-gamma) and its location. The operator can then conduct a more thorough investigation. If the alarm is determined to be false or the condition corrected, the operator commands the robot to resume operation.

Once a path is downloaded from the host computer, the robot conducts a floor survey autonomously, as opposed to prior art techniques that require continuous operator supervision. The robot can maintain a predetermined scanning speed (typically about 1"/sec or 2.5 cm/sec) and perform around the clock. Thus, the robot can survey a greater surface area more thoroughly than is possible for a human operator.

An important feature of the present invention is the use of a programmed-path, autonomous robot to perform routine radiological surveys. The robot is programmed to follow a predefined path through an area to be surveyed for floor-level contamination. The program may be for a relatively simple path such as moving up and down a single hallway, or a more complex path such as scanning in succession the floors of several rooms, hallways, nuclear storage or spill sites, and so forth. The presence of unprogrammed points representing objects such as humans working in the area, small items of furniture, boxes, and so forth does not affect the robot's performance of its assigned task: its collision avoidance system allows it to operate safely in the presence of humans or inanimate objects. Furthermore, an autonomous robot can operate during off hours so there is mininal disturbance to the activities of the facility where the robot is surveying. Also, the robot is more reliable in that it can survey at any preselected rate over any preprogrammed area without fail.

Another feature of the present invention is the onboard computer system. The system includes an integrator that provides an interface between the radiation monitor and the robot, and three dedicated units used to control the movement of the robot: a navigation computer, a collision avoidance computer, and a docking beacon computer. The collision avoidance computer interfaces with the outputs of the ultrasonic transducers and provides information on obstacle ranges. The docking beacon computer is used primarily to calibrate the position and heading of the robot during docking and also controls the robot for accurate docking. This computer system enables the robot to respond with intelligence in performing its responsibilities.

Still another feature of the present invention is the radiation monitor. The monitor is preferably a microcomputer-based multi-channel unit that can be interfaced with a plurality of detectors to detect alpha, beta-gamma and other radiation such as neutron or gamma-only radiation. It can compare pulse count rates to preselected rates for determining whether an alarm is to be sounded. The detector has two downward-facing detectors to monitor floor-level contamination and a third detector facing upwards to detect background radiation. The upward-facing detector is shielded from the downward-facing detectors.

Another feature of the invention is the positioning of the ultrasonic transducers. The transducers sense the presence and location of obstacles by echolocation, allowing the robot to safely navigate around these obstacles. Two transducers are located on the front of the robot, two on the rear, and one on each side. The front transducers are located at the ends of rods extending forward approximately one foot (30.5 cm) from the robot. Thus, the transducers do not have to "see" as far to avoid obstacles in the path of the robot.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a perspective, partially cut-away view of an apparatus according to a preferred embodiment of the present invention;

FIG. 3 is a side view of an apparatus and a docking station according to a preferred embodiment of the present invention; and FIG. 4 is a block diagram of the computer systems of the apparatus of FIG. 1.

DETAILED DESCRIPTION OF A PREFERRED EMBODIMENT

Figure 2A:
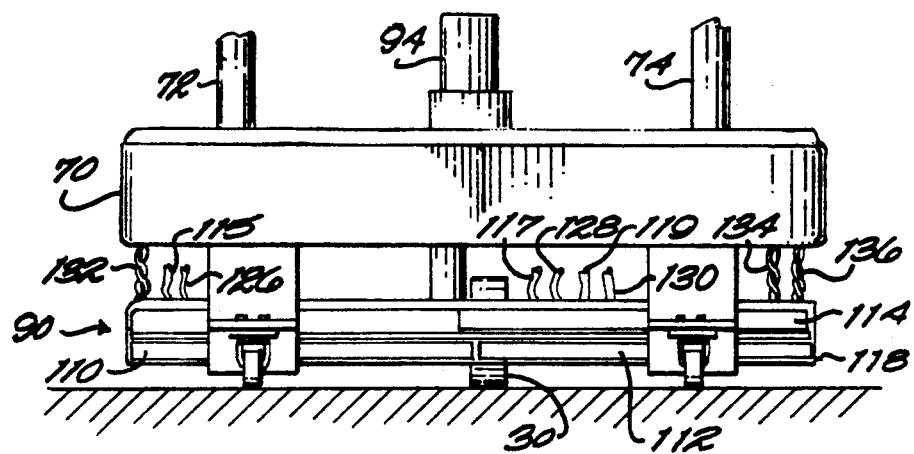
FIG. 2A is a front view of the radiation detector assembly of the apparatus of FIG. 1.
Figure 2B:
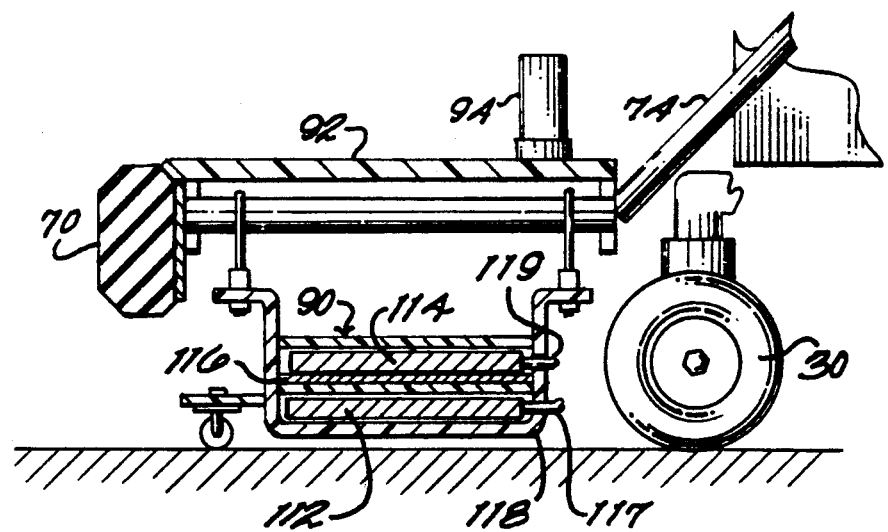
FIG. 2B is a side view of the radiation detector assembly of FIG. 2A.

Referring now to FIG. 1, there is shown a perspective view of an apparatus for conducting radiologic surveys according to a preferred embodiment of the present invention. Autonomous mobile robot 10 has base 12 with rotatable module 14. Module 14 has a turret 16 and strobe light 18. If desired, module 14 also has a microwave antenna 20 for transmitting signals from a video camera (not shown) to a remote receiver.

Robot 10 is an autonomous unit that can follow a preprogrammed path through an area. Robot 10 may incorporate a commercially-available robot platform, such as the K2A Navmaster, a semi-intelligent mobile robot made by Cybermotion of Roanoke, VA. The Navmaster is a three-wheeled vehicle weighing about 300 pounds and powered by a rechargeable 24-volt DC battery. The three wheels are synchro-driven so that they turn in unison and trace parallel paths. As a result, the vehicle has a zero turning radius and large tractive forces. The unit has an interface for user-installed subsystems, slots for a docking beacon and autocharging receptacle, and mounts for bumper guards. Alternatively, robot 10 may have any suitable mobile base that provides similar capabilities.

Base 12 has three wheels 30, switches 32 and panel 34. Switches 32 are on-off switches, preferably pushbutton switches, that allow an operator to manually stop the movement of robot 10. Panel 34 contains fuses, connections for diagnostic equipment, and so forth. Base 12 houses a motor, a battery, and some controls for operating robot 10. Wheels 30 lock and drive in synchronization. The circumference of wheels 30 is known; the orientation of wheels 30 at any given time is also known. Therefore, the distance traveled by robot 10 is determined simply by counting revolutions of wheels 30 with wheels 30 oriented in one direction. Robot 10 navigates by dead reckoning, that is, by computing its position from known directions and distances traveled, with adjustments as explained below.

Module 14 has left side 40, right side 42, front 44, and rear 46 (FIGS. 1,3). Sides 40, 42 carry ultrasonic transducers 48, 50, respectively. Front 44 and rear 46 each has a pair of ultrasonic transducers 52, 54 respectively. Front transducers 52 are extended forward by mounting them on rods 56, as best seen in FIG. 1. Front 44 also has charging socket 60 and infrared detector 62. Module 14 is equipped with several on-board computers (not shown).

Ultrasonic transducers 48, 50, 52, 54 are preferably wide-beam piezoelectric transducers operating at a frequency of approximately 75 kHz. This operating frequency allows for the detection of relatively small objects by echo-location and avoids interference from other, lower-frequency sources. The transducers sense objects as small as ¼" (about 0.6 cm) in diameter that are between 4" (about 10 cm) and 5' (about 150 cm) above the floor. Paired front transducers 52 and rear transducers 54 provide a stereoscopic "view" of the forward and rearward direction of travel of robot 10, giving better positioning capability to robot 10. To conserve energy, rear transducers 54 only operate when robot 10 is backing up.

Side transducers 48, 50 are used for advanced navigation functions, including wall following, hall following, and circumnavigation. Robot 10 uses side transducers 48, 50 to maintain its distance from a wall in order to move parallel to that wall. By "pinging" the wall a number of times, robot 10 collects a series of distance data points that should fit a line in order to be recognized as a "wall." The slope of the line should be zero if robot 10 is moving parallel to it. If a door or other wall feature is found, robot 10 ignores the new data points and uses dead reckoning until it finds a valid "wall." Hall following is done using both walls of a hall to maintain position. Robot 10 uses circumnavigation to go around an object in its path. Input from front transducers 52, side transducers 48, 50, and rear transducers 54 is used to plan a path around the obstacle. For good coverage of a surface to be samples, the speed of robot 10 is preferably in the range of about 1"/sec (about 2.5 cm/sec).

Radiation monitor 64 is housed in module 14. Monitor 64 is preferably a microcomputer-based multi-channel unit that can be interfaced with a plurality of detectors to detect alpha, beta-gamma and other radiation such as a monitor manufactured by the Eberline division of Thermo Instrument Systems, Inc. of Santa Fe, N. Mex. This monitor can be used with proportional, scintillation, or Geiger-Mueller detectors, and includes amplifier-discriminator and power supply boards for the detectors. Monitor 64 preferably has at least five channels (alpha left, beta-gamma left, alpha right, beta-gamma right, beta-gamma upward), for three radiation detectors, as discussed below. It can store data for such purposes as comparing pulse count rates to preselected rates for determining whether an alarm is to be sounded. If desired, monitor 64 includes digital readout 66 providing a continuous display of the overall system status, keypad 68 for entering/editing the system operating parameters, an audible alarm, indicator lights to indicate measurement status, and system diagnostics to self-test the system and perform statistical measurements of detector performance. Monitor 64 preferably has at least one serial I/O port for computer control.

Front bumper 70 is attached to module 14 by bumper mounts 72, 74; rear bumper 76 is attached by bumper mounts 78, 80. Bumpers 70, 76 are preferably highly compliant, serving as an additional safety system and backup to the collision-avoidance system of robot 10. When bumper 70 or bumper 76 contacts an object, limit switches (not shown) stop robot 10. Motion does not resume until the limit switches return to their normal positions. Radiation detector assembly 90 and cover 92 are attached to front bumper 70. A strobe light 94, preferably a red light, is mounted in cover 92.

Front ultrasonic transducers 52 are mounted on rods 56, and extend outwards from front 44, as best seen in FIG. 1. Thus, front transducers 52 are positioned above detector assembly 90, for more efficient sensing of obstacles in front of assembly 90.

Turret 16 contains gas cylinders 96, 98 that provide a supply of gas to radiation detector assembly 90. Cylinders 96, 98 are surrounded by housing 100 and covered by cap 102.

Radiation detector assembly 90 includes, preferably, two downward-facing detectors 110, 112 and an upward-facing detector 114 (FIG. 2a). Detectors 110, 112, and 114 are preferably gas proportional counters, but may be some other type of detector with the desired radiation-detecting capabilities.

Detectors 110 and 112 are arranged side-by-side and facing downwards to detect floor-level contamination. Detectors 110 and 112 are close to the floor for sensitivity to alpha radiation, preferably approximately 0.5" (1.3 cm) above the floor surface. Detector 114 faces upwards to detect background radiation, particularly gamma radiation. To prevent detector 114 from detecting floor contamination, detector 114 is shielded from detectors 110 and 112 by shield 116. Detectors 110, 112, and 114, and shield 116 are carried by frame 118.

Cylinders 96, 98 supply a purge of approximately 30 cc/min to detectors 110, 112, and 114 of assembly 90. Cylinders 96, 98 contain P-10 gas, a mixture of 90% argon and 10% methane, needed for efficient detection because radiation ionizes the gas more readily than it does free air. Detectors 110, 112, and 114 are connected to cylinders 96, 98 by gas input lines 115, 117, and 119, respectively. Gas is transferred from the detectors by output lines 126, 128, and 130. Electrical cables 132, 134, and 136 connect the detectors to a power supply (not shown) carried by base 12.

Robot 10 is stored at docking station 120 when not in use, resting on grounded metal plate 122 (FIG. 3). Docking station 120 includes infrared beam generator 124 and charging prong 126. Robot 10 docks itself at station 120 for recharging, guided by infrared detector 62 and an infrared beam from generator 124. Detector 62 has at least one, and preferably four, infrared receivers that are used to align robot 10 with docking station 120. Charging prong 126 is adapted to recharge a 24-volt DC battery (or other battery used to power robot 10), and interfaces with socket 60 to recharge robot 10. Alternatively, robot 10 is powered by a replaceable battery pack.

Plate 122 is grounded to the foundation of the area where robot 10 is used. Robot 10 has a plurality of metal grounding tapes 130 for discharging static electricity built up during movement over nonconducting floors. Grounding tapes 130 have resistors connected in line to prevent damage to computers carried by robot 10.

Robot 10 navigates by dead reckoning during normal operations, as described above. This technique enables robot 10 to sense its position to about 0.01' (0.3 cm) with an accuracy of about 0.5%. Dead reckoning is highly accurate in providing information on the linear distance traveled by robot 10. Wall following is thus the most powerful navigation tool used by robot 10. However, dead reckoning is sensitive to heading error. Small positioning errors may accumulate, due primarily to the wheel slippages encountered when robot 10 executes turns. Docking station 120 therefore includes a narrow beam ultrasonic transducer (not shown), used by robot 10 to obtain range information with respect to station 120.

In a complexly structured area, robot 10 can also correct its position by using sonic markers, small sheets of metal attached to walls, corners, and so forth at known locations. The markers return strong ultrasonic reflections to transducers 48, 50, 52, and 54, serving as landmarks for robot 10. When robot 10 "pings" a marker, it corrects its position coordinates using the distance and direction from itself to the known position of the marker.

Robot 10 is equipped with on-board computer system 150. The individual computers of system 150 are preferably all based on the same central processing unit, such as a Z-80 or similar chip. Thus, the computers are all able to use the same communications software. Computer system 150 includes three dedicated units used to control the movement of robot 10: navigation computer 152, collision avoidance computer 154, and docking beacon computer 156 (FIG. 4). Collision avoidance computer 154 interfaces with the outputs of ultrasonic transducers 48, 50, 52, and 54. It processes raw data from the transducers and provides information on obstacle ranges. Docking beacon computer 156 is used primarily to calibrate the position and heading of robot 10 when robot 10 attempts to dock with station 120. Integrator 158 provides an interface between radiation monitor 64 and robot 10. Alternatively, robot 10 is supplied with a single on-board computer having the capacity to perform all of these functions.

Two internal communications links connect robot 10 with a remotely-located host computer: supervisory link 160 and control link 162 (FIG. 4). Typically, the host acts as the "master" computer and the on-board computers act as "slaves" on the supervisory link. All the on-board computers reside on supervisory link 160. The host uses supervisory link 160 to download programs, monitor performance and control the modes of operation of the slave computers. To avoid contention among the slave computers for access via the bus to the host computer, the host can interrogate any slave computer on its link for data while a slave can only talk when interrogated. However, a slave computer with high enough priority can assert a "port request" line on the bus. For example, if integrator 158 detects an alarm condition on radiation monitor 64, it immediately becomes bus master and issues a "halt" message. It then releases the port request line to allow the host or other computers to become the bus master.

Control link 162 synchronizes navigation-related events during autonomous operation of robot 10. Navigation computer 152 is the master on control link 162. Collision avoidance computer 154 and docking computer 156 reside on control link 162 and act as slaves. When the host sends directions for an autonomous mission to robot 10, these directions are stored in navigation computer 152 in the form of a program. As navigation computer 152 steps through the program, it continuously reads the information on obstacle ranges provided by collision avoidance computer 154 and modifies the speed of robot 10 accordingly. During docking, navigation computer 152 communicates with collision avoidance 154 and docking computer 156.

The host includes two computers: first host computer 170 runs communications software for programming robot 10, and second host computer 172 monitors radiation monitor 64. Host 170 sends information to robot 10 via UHF radio link 174; robot 10 receives transmitted information on radio link 176 (FIG. 4). To program robot 10, the operator first defines valid points in the area where robot 10 is to operate. Programmed points may define the features of the area: the locations of walls, doors, stationary furniture and equipment, sonic markers if used, and so forth. Point-to-point path programs consisting of simple commands and parameters pertinent to navigation are written and assembled into "action files." Then, if the operator commands robot 10 to go from point "a" to point "b," the program sorts through its database of action files to find a path between the points. If there is no straight path between the points, the program merges several action files in an attempt to find a valid path. If multiple paths exist, host computer 170 downloads the most efficient path to robot 10 via radio links 174, 176. If desired, the program may include a path-planning menu that allows the operator to plan a path before robot 10 is dispatched on a mission. Another menu might provide the operator with a map of the area with a graphical representation of the position and orientation of robot 10 relative to the area. Once a program has been downloaded to robot 10, the robot operates even if host computer 170 is disconnected. However, if computer 170 remains in communication with robot 10, the host can display the position of robot 10 and other parameters such as the output of radiation monitor 64 during operation.

Second host computer 172 monitors the activity of radiation monitor 64 and radiation detectors 110, 112, and 114. Hosts 170 and 172 communicate with robot 10 through link arbitrator 180 and UHF radio linkage 174 (FIG. 4). Robot 10 has two modes of operation, manual and automatic. In manual mode, an operator directs the motion of robot 10 via a joystick connected to link arbitrator 180. In automatic mode, host 170 is master of the link and robot 10 executes a predefined path downloaded to navigation computer 152. Once a path is downloaded to robot 10, the robot acts autonomously until it reaches the end of the path. Thus, actual path planning is done by host computer 170, not by robot 10. Second host computer 172 may request the link, however, computer 172 must relinquish the link when its task is completed. By way of example, host 172 requests the link at regular intervals to check on the status of radiation monitor 64. If no contamination is present, host 172 relinquishes the link. If contamination is present, host 172 outputs a message indicating the presence of contamination along with the position of robot 10.

In either mode of operation, host computer 170 provides a map showing the position and orientation of robot 10, together with other parameters such as battery voltage, motor currents, and various obstacle ranges.

Integrator 158 communicates with radiation monitor 64 through a serial port, and constantly monitors the outputs of monitor 64 that signal high radiation levels. Strobe light 18 is turned on during operation of robot 10. If integrator 158 senses an alarm condition on one or both of downward-facing detectors 110, 112, it immediately sends a "halt" message to navigation computer 152 by asserting its port request line and becoming the temporary master of supervisory link 160. Robot 10 stops and flashes red strobe light 94.

Robot 10 then backs up a short distance (about 6" or 15 cm) and resurveys the area at reduced speed (about 0.5"/sec; 1.3 cm/sec) to confirm the presence of contamination. If no contamination is found on the second pass, robot 10 resumes its preprogrammed path. If the contamination is confirmed, robot 10 stops, flashes strobe light 94 continuously and sounds an audible alarm. A "contamination present" message is flashed on the display screen of host computer 172, together with the position coordinates of robot 10. The robot also simulates speech telling which detector has sensed contamination and which type of contamination is present (alpha or beta/gamma). Robot 10 remains stationary until an operator provides an "alarm acknowledge" signal, preferably by manually pushing an alarm button on keypad 68 located on robot 10. This causes robot 10 to back up about 1' (about 30 cm), and activates a voice synthesizer 178 that outputs a message indicating the type of contamination detected (alpha or beta-gamma) and its location (detector 110 or detector 112). The operator can then conduct a more thorough investigation with more sensitive equipment. If the alarm is determined to be false, the operator resumes operation of robot 10 by pressing the "alarm acknowledge" button once again, prompting integrator 158 to send a "resume" message to navigation computer 152. Thus, no path replanning and downloading is needed. Robot 10 resumes its mission on its own initiative rather than from the remotely-located host computers 170, 172. Robot 10 returns to docking station 120 at the completion of a survey mission, when it needs recharging, and for recalibration of its position.

Integrator 158 performs other functions as well. Periodically, it directs robot 10 to update the background pulse rates measured by detector 114. To update the background count, robot 10 stops, then waits for several seconds (preferably at least 10 seconds) while monitoring the outputs of downward-facing detectors 110, 112. Once it is clear that there is no contamination on the surface beneath detectors 110, 112, integrator 158 proceeds to sample the background data. This data is fed to monitor 64 as reference data, and is subtracted from each count. The background is continuously sampled and compared to preselected narrow limits by monitor 64. If these limits are exceeded, the background levels are remeasured and the new background count is used as a reference. If desired, the background count may be updated at regular intervals, such as once per hour.

When robot 10 is initially activated, detector 114 monitors the background radiation for several seconds to update its stored data on the background radiation level of the area. Detector 114 triggers an alarm condition if the background radiation level changes significantly thereafter. If this occurs, robot 10 stops and updates the background levels before resuming its survey mission.

Integrator 158 monitors gas flow from cylinders 96, 98. For most efficient operation, gas must be supplied to and purged from the proportional counters (detectors 110, 112, 114) continuously. If one cylinder empties, integrator 158 activates a solenoid valve (not shown) to direct gas from the other cylinder to the detectors.

Integrator 158 also detects the presence of loose cables, insufficient gas in cylinders 96, 98, failure of detectors 110, 112, and 114, and other unplanned events. Some events, such as insufficient gas in one of cylinders 96, 98, can be fixed by integrator 158. Others, such as a loose cable or a failed detector, require the attention of a human operator. When such unfixable events occur, robot 10 simply stops and notifies either or both of host computers 170, 172 of its condition.

Robot 10 is programmed to follow a pre-determined path via host computer 170 that downloads the program to on-board computer system 150. Programs may be for relatively simple tasks calling on a small number of pre-programmed action files, such as moving up and down a single hallway to detect floor-level contamination. Programs may include more complex routines requiring robot 10 to use a large number of action files, such as scanning in succession the floors of several rooms, hallways, nuclear storage or spill sites, and so forth. Typically, the environment where robot 10 operates is made up of well-defined, unobstructed smooth surfaces. Therefore, programming the paths that robot 10 is to follow is a straightforward task. If the environment changes, perhaps as the result of moving furniture or equipment, the new features are readily input into robot 10's preprogrammed data. Old action files are erased or corrected, as needed, and new action files are added for new features. The presence of "unknown" objects such as humans working in the area, small items of furniture, boxes, and so forth does not affect robot 10's performance of its assigned task: its collision avoidance system allows the robot to operate safely in the presence of humans or inanimate objects.

Once programmed, robot 10 conducts floor surveys autonomously, as opposed to prior art techniques that require continuous operator supervision. It performs more reliably than a human operator—conducting scanning of a floor at 1"/sec (about 2.5 cm/sec) is an extremely tedious and time-consuming task. Unlike a human operator, robot 10 can maintain its speed and perform around the clock, thus covering more surface area. Robot 10 may be programmed to conduct surveys on a periodic basis. To reduce pedestrian interference, the surveys may be performed at night.

If desired, on-board computer system 150 can be outfitted with memory boards for storage of radiation data. After each counting cycle, integrator 158 reads the position of robot 10 from navigation computer 152 and the counts of detectors 110, 112, and 114 over the serial link. Integrator 158 compresses this data and stores it in nonvolatile RAM memory. Approximately 1 megabyte of RAM memory can store data from up to 48 hours of continuous, uninterrupted operation of robot 10. After robot 10 completes a survey, this data is downloaded over radio links 174, 176 and stored on host computer 172. The data can then be processed to provide a radiation contour map of a contaminated or potentially contaminated area. Such characterization of the area can be a powerful tool for decontamination and decommissioning purposes. For example, a radiation map of an area would facilitate efficient allocation of resources so that regions of known contamination could be treated more aggressively than relatively "clean" regions.

It will be apparent to those skilled in the art that many changes and substitutions can be made to the preferred embodiment herein described without departing from the spirit and scope of the present invention as defined by the appended claims.

What is claimed is:

1. An apparatus for performing radiological surveys, said apparatus measuring the level of radiation on a surface and indicating when said surface radiation exceeds a predetermined level, said apparatus comprising:
    a vehicle;
    means carried by said vehicle for locating objects in the path of said vehicle;
    means for detecting radiation, said detecting means carried by said vehicle in spaced relation to said surface so that said detecting means can measure said level, said detecting means producing a first output responsive to said measured level;
    means responsive to said detecting means for monitoring said first output, said monitoring means carried by said vehicle and producing a second output when said first output exceeds a preselected limit; and
    means responsive to said monitoring means for controlling the movement of said vehicle, said controlling means carried by said vehicle and automatically directing said vehicle to remeasure said surface when said monitoring means produces said second output.

2. The apparatus as recited in claim 1, further comprising an alarm carried by said vehicle and wherein said controlling means activates said alarm when said monitoring means produces said second output after said surface has been remeasured.

3. The apparatus as recited in claim 1, further comprising:
   an alarm carried by said vehicle; and
   means carried by said vehicle for generating an alarm acknowledgement signal, and wherein said controlling means activates said alarm when said monitoring means produces said second output after said surface has been remeasured and backs said vehicle when said alarm acknowledgment signal is generated.

4. The apparatus as recited in claim 1, wherein said locating means further comprises a plurality of transducers held forward of and away from said vehicle.

5. The apparatus as recited in claim 1, wherein said detecting means comprises:
   at least one gas proportional counter, and
   a supply of gas in fluid communication with said at least one gas proportional counter,
   said controlling means controlling said supply of gas to said at least one gas proportional counter.

6. The apparatus as recited in claim 1, wherein said detecting means comprises:
   at least one gas proportional counter;
   at least two tanks of gas; and
   hoses running from said at least one gas proportional counter to said at least two tanks of gas,
   said controlling means controlling supply of said gas to said at least one gas proportional counter from said at least two tanks of gas and switching from one tank of said at least two tanks of gas to another tank of said at least two tanks when said one tank is empty.

7. The apparatus as recited in claim 1, wherein said detecting means further comprises:
   at least one first detector facing said surface;
   at least one second detector facing away from said surface for detecting background radiation; and
   shielding between said at least one first detector and said at least one second detector.

8. An apparatus for performing radiological surveys, said apparatus measuring the level of radiation on a surface and indicating when said surface radiation exceeds a predetermined level, said apparatus comprising:
   a vehicle;
   means for navigating said vehicle over said surface, said navigating means adapted to direct said vehicle to follow a preselected path;
   a plurality of transducers carried by said carried by said vehicle for locating objects in said preselected path;
   means for detecting radiation, said detecting means carried by said vehicle in spaced relation to said surface so that said detecting means can measure said level, said detecting means producing a first output responsive to said measured level;
   means responsive to said detecting means for monitoring said first output, said monitoring means carried by said vehicle and producing a second output when said first output exceeds a preselected limit; and
   means carried by said vehicle in operating connection with said monitoring means, said navigating means and said plurality of transducers for integrating movement of said vehicle by said navigating means with said monitoring means and said plurality of transducers, such that said integrating means directs said detecting means to remeasure said surface in response to receipt of said second output from said monitoring means.

9. The apparatus as recited in claim 8, wherein said integrating means directs said vehicle to back up and said detecting means to remeasure said surface in response to receipt to said second output from said monitoring means.

10. The apparatus as recited in claim 8, further comprising an alarm carried by said vehicle and wherein said integrating means directs said vehicle to back up and remeasure said surface in response to receipt to said second output, said integrating means activating said alarm in response to receipt of said second output from said monitoring means after said detecting means has remeasured said surface.

11. The apparatus as recited in claim 8, further comprising:
   an alarm carried by said vehicle; and
   means carried by said vehicle for generating an alarm acknowledgment signal,
   said integrating means directing said vehicle to back up and remeasure said surface in response to receipt to said second output and activating said alarm in response to receipt of said second output from said monitoring means after said detecting means has remeasured said surface, said integrating means directing said vehicle to back up a second time in response to receipt of said alarm acknowledgment signal.

12. The apparatus as recited in claim 8, wherein said detecting means comprises:
   at least one gas proportional counter;
   at least two tanks of gas; and
   hoses running from said at least one gas proportional counter to said at least two tanks of gas,
   said integrating means controlling supply of said gas to said at least one gas proportional counter from said at least two tanks of gas and switching from one tank of said at least two tanks of gas to another tank of said at least two tanks when said one tank is empty.

13. The apparatus as recited in claim 8, wherein said detecting means further comprises:
   at least one first detector facing said surface;
   at least one second detector facing away from said surface for detecting background radiation; and
   shielding between said at least one first detector and said at least one second detector.

14. The apparatus as recited in claim 8, wherein said detecting means comprises:
   a first gas proportional counter facing said surface;
   a second gas proportional counter facing away from said surface;
   shielding between said first and said second gas proportional counters
   at least two tanks of gas; and
   hoses running from said first and said second gas proportional counters to said at least two tanks of gas,
   said integrating means controlling supply of said gas to said first and said second gas proportional counters from said at least two tanks of gas and switching from one tank of said at least two tanks of gas to another tank of said at least two tanks when said one tank is empty.

15. The apparatus as recited in claim 8, wherein said plurality of transducers is held forward of and away from said vehicle.

16. The apparatus as recited in claim 8, further comprising means for identifying via synthesized speech the type of radiation detected by said detecting means.

17. An apparatus for performing radiological surveys, said apparatus measuring the level of radiation on a surface and indicating when said surface radiation exceeds a predetermined level, said apparatus comprising:
a vehicle;
a battery for powering said vehicle;
means for navigating said vehicle over said surface, said navigating means including a first plurality of transducers carried by said vehicle adapted to direct said vehicle to follow a preselected path;
a second plurality of transducers carried by said vehicle for locating objects;
means for detecting radiation, said detecting means carried by said vehicle in spaced relation to said surface so that said detecting means can measure said level, said detecting means producing a first output responsive to said measured level;
means responsive to said detecting means for monitoring said first output, said monitoring means carried by said vehicle and producing a second output when said first output exceeds a preselected limit;
an alarm carried by said vehicle; and
means carried by said vehicle in operating connection with said monitoring means, said navigating means and said second plurality of transducers for integrating movement of said vehicle by said navigating means in response to said output of said monitoring means and said second plurality of transducers, said integrating means directing said detecting means to remeasure said surface in response to receipt of said second output and activating said alarm if said monitoring means produces said second output after said remeasuring.

18. The apparatus as recited in claim 17, wherein said detecting means comprises:
a first gas proportional counter facing said surface;
a second gas proportional counter facing away from said surface;
shielding between said first and said second gas proportional counters
at least two tanks of gas; and
hoses running from said first and said second gas proportional counters to said at least two tanks of gas,
said integrating means controlling supply of said gas to said first and said second gas proportional counters from said at least two tanks of gas and switching from one tank of said at least two tanks of gas to another tank of said at least two tanks when said one tank is empty.

* * * * *